US00PP18111P3

(12) United States Plant Patent
Khanizadeh

(10) Patent No.: US PP18,111 P3
(45) Date of Patent: Oct. 9, 2007

(54) STRAWBERRY PLANT NAMED 'SAINT-JEAN D'ORLEANS'

(50) Latin Name: *Fragaria×ananassa Duch.*
Varietal Denomination: Saint-Jean d'Orleans

(75) Inventor: Shahrokh Khanizadeh, Baie d'Urfé (CA)

(73) Assignee: Her Majesty the Queen in Right of Canada, as represented by the Minister of Agriculture and Agri-Food Canada, Saint-Jean-Sur-Richelieu (CA)

( * ) Notice: Subject to any disclaimer, the term of this patent is extended or adjusted under 35 U.S.C. 154(b) by 271 days.

(21) Appl. No.: 10/941,875

(22) Filed: Sep. 16, 2004

(65) Prior Publication Data

US 2006/0059592 P1 Mar. 16, 2006

(51) Int. Cl.
*A01H 5/00* (2006.01)

(52) U.S. Cl. ..... Plt./208
(58) Field of Classification Search ..... Plt./208
See application file for complete search history.

(56) References Cited

PUBLICATIONS

Upov–rom GTITM, Plant Variety Database, 2006/01, GTI Jouve Retrieval Software, Citation for *Fragaria* 'Saint–Jean d'Orleans' one page.*
Baldwin E.A. et al. 1995. Use of edible coatings to preserve quality of lightly processed products. Crit. Rev. Food Sci. Nutr. 35:509–24.
Gao, X. et al. 2000. Changes in antioxidanants effects and their. . . (Hyppophae rhamnoides L) during maturation. J. Agric Food Chem. 48:1485–1490.
Khan, S.H. et al. 1999. The potential for anti–oxidant chemicals to control. . . 51 International Symposium on Crop Protection. Gent (Belgium). V.64 (3b): 531–537.
Khanizadeh, S., B. Thériault, O. Carisse and D. Buszard. 1999. AC–'Acadie Strawberry. HortScience 34(4):743–744.
Linhard Pedersen. 2003. http://www.darcof.dk/research/darofi/ii1.html.
Mayr, U. et al. 1997. Phenolic compounds of apple and their relationship to scab resistance. J. Phytopathology 145: 69–75.
Nicholson, R.L.et al. 1992. Phenolic compounds and their role in disease resistance. Annu. Review Phytopathology 30:369–389.
Slinkard, K. et al. 1977. Total phenol analysis: automation and comparison with manual methods. Am. J. Enol. Viticult. 28:49–55.
Tsao, R. et al. 2003. Optimization of a new mobile phase to know the complex. . . J. Chromatogr. A. 1018:29–40.
Tsao, R., et al. 2003. Antioxidant isoflavones in Osage Orange, Maclura pomifera (Raf.) Schneid. J. Agric. Food Chem. 51: 6445–6451.
Wang, S.Y. et al. 1994. Ellagic acid in small fruits, mayhaws, and other plants. J. Small Fruit and Viticulture 2 (4): 39–49.

* cited by examiner

*Primary Examiner*—Kent Bell
*Assistant Examiner*—June Hwu
(74) *Attorney, Agent, or Firm*—Goudreau Gage Dubuc

(57) ABSTRACT

A new and distinct June-bearing strawberry cultivar named 'Saint-Jean d'Orléans' is primarily adapted to the growing conditions of Eastern Central Canada. Its high yield of medium sized, firm, light-red glossy fruits, resistance to leaf diseases, long shelf life and high levels of given antioxidants essentially characterize 'Saint-Jean d'Orléans'.

4 Drawing Sheets

Botanical designation: *Fragaria×ananassa* Duch.
Variety denomination: 'Saint-Jean d'Orléans'.

FIELD OF THE INVENTION

The present invention relates to a new and distinct June bearing strawberry cultivar designated as 'Saint-Jean d'Orléans'. This cultivar belongs to the genus *Fragarias* (*×ananassa* Duch.), whose fruit are juicy, edible and usually red, and is cultivated for culinary purposes.

BACKGROUND OF THE INVENTION

The new cultivar, tested as FIO9623-43, is the progeny of a cross made by Shahrokh Khanizadeh 'L'Acadie'[1] and 'Joliette' (U.S. Plant Pat. No. 10,460). 'L'Acadie' is a June bearing strawberry cultivar (*Fragaria×ananassa* Duch.) bred for Eastern Central Canada and more specifically for Quebec growing conditions. 'L'Acadie' is noted for large, firm fruits, moderate resistance to leaf diseases, partial resistance to red stele (*Phytophthora fragariae* Hickman), and keeping quality of several days after picking or maturity in the field. 'Joliette' has high yields of large, moderately firm fruits and is resistant to leaf spot (*Mycosphaerella fragariae* Tul.) and to six North American eastern (NAE) races of red stele (*Phytophthora fragariae* Hickman).

The cross took place in 1993 in St-Jean-sur-Richelieu, Québec. The 'Saint-Jean d'Orléans' strawberry was asexually propagated by runners in L'Acadie, Québec and extensively tested at the same location, where it has been tested since 1997. Selection criteria included shelf life, yield, fruit size and color, and disease resistance. It was further tested in semi-commercial sites in Saint Laurent, Île d'Orléans, Québec, Canada and in Kent, UK. 'Saint-Jean d'Orléans' is now an established and stable cultivar.

BRIEF SUMMARY OF THE INVENTION

'Saint-Jean d'Orléans' is recommended for Eastern Central Canada, especially in areas where the climate is similar to that in the strawberry production areas of Quebec, such as l'Île d'Orléans. Typically, strawberry production in Quebec occurs in areas with winter temperatures down to −30° C. and warm and humid summers with unpredictable mixture of sun and rain (drought some seasons, constant rain other seasons). The high yield of medium sized, firm, light-red glossy fruits (FIG. 2), resistance to leaf diseases, long shelf life and high levels of given antioxidants essentially characterize 'Saint-Jean d'Orléans', as compared to the well-known variety 'Kent' for example. The fruits of 'Saint-Jean d'Orléans' are ideal for pick your own, fresh market and shipping.

BRIEF DESCRIPTION OF THE DRAWINGS

The accompanying color photographs show typical specimens of the new variety at various stages of development as nearly true as it is possible to make in color reproductions.

DETAILED BOTANICAL DESCRIPTION

Figure 1:
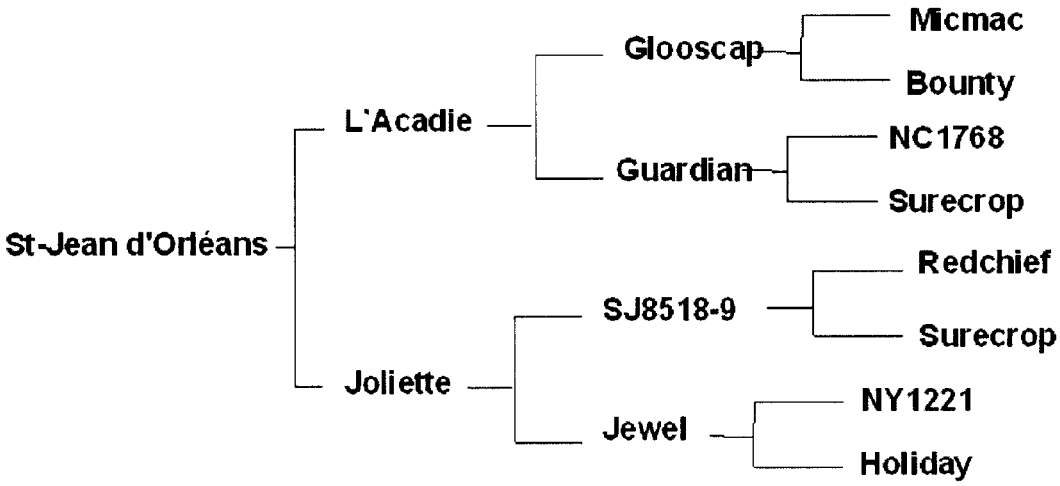
FIG. 1 shows a schematic pedigree of 'Saint-Jean d'Orléans'.
Figure 2:
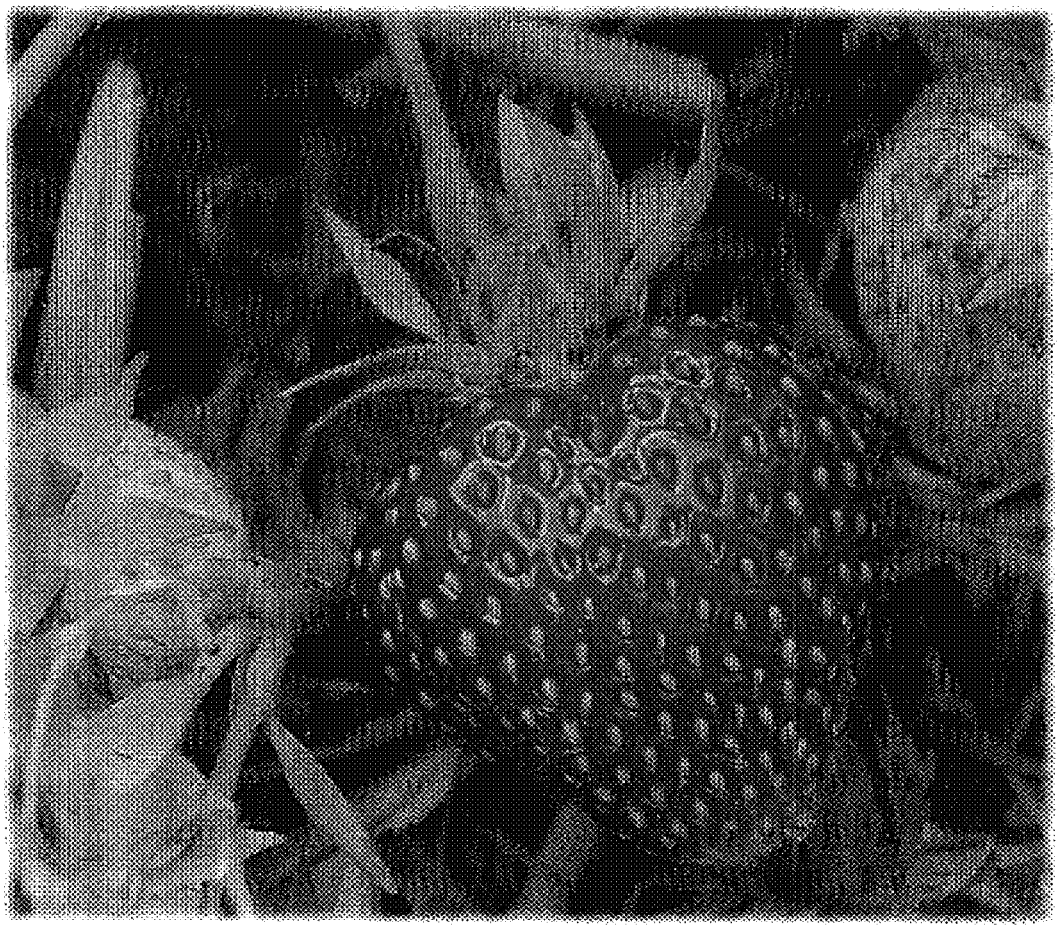
FIG. 2 shows a close-up view of 'Saint-Jean d'Orléans' fruits.
Figure 3:
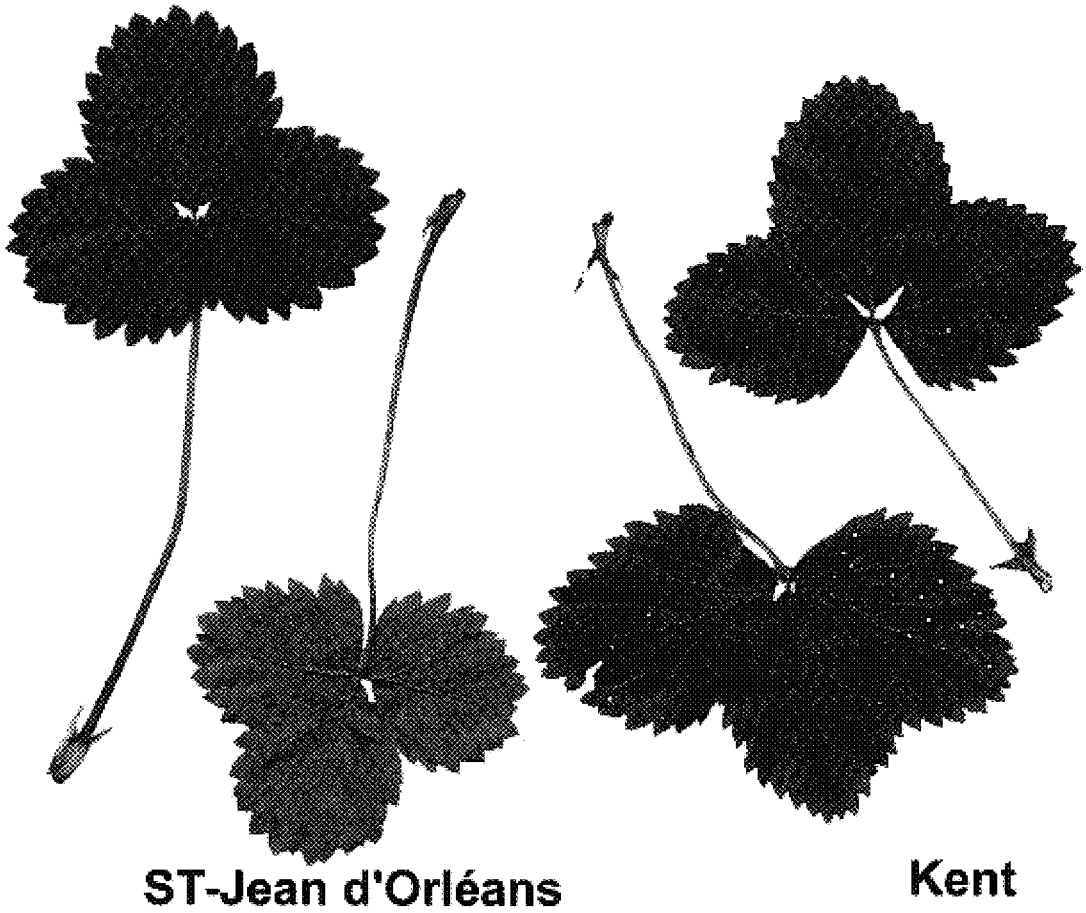
FIG. 3 shows a comparison of trifoliates between 'Saint-Jean d'Orléans' and 'Kent'.
Figure 4:
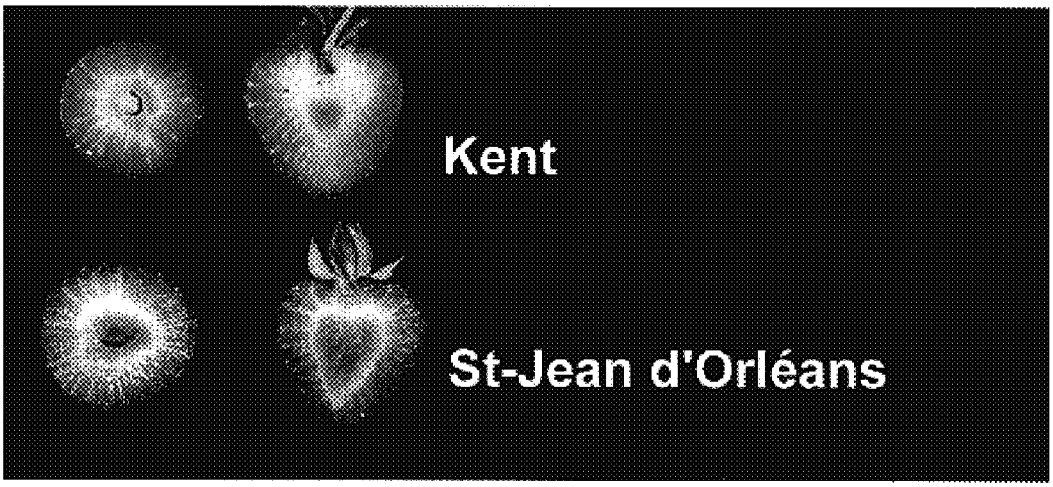
FIG. 4 shows a comparison of internal fruit characteristics between 'Saint-Jean d'Orléans' and 'Kent'.

'Saint-Jean d'Orléans' is a June bearing strawberry cultivar (*Fragaria×ananassa* Duch.) with early flowering date and harvest maturity. It is a progeny (FIO9623-43) resulting from a cross between two recent releases, 'L'Acadie' and 'Joliette'. 'Saint-Jean d'Orléans' is vigorous, produces high yields of medium, firm, light-red to red colored fruits and performs a longer storage life than the standard variety 'Kent', used by many growers. It shows resistance to leaf diseases and levels of antioxidants that are higher than those of 'Kent', which makes it ideal for growers who need to store the fruits for several days or ship them to other provinces for marketing. Color reference are made to The Royal Horticulture Society Colour Chart (R.H.S.), except where general terms of dictionary significance are used.

The selection was named after the village of Saint-Jean d'Orléans, which is located on south-eastern side of l'Île d'Orléans, Quebec. In this area, the principal economy comes from agriculture, with a major emphasis on vegetable and strawberry production. This village is known as a capital of strawberry production in Quebec and is recognized for a high quality fruit production.

Plants of 'Saint-Jean d'Orléans' are vigorous, have a flat growing habit, and produce 4–5 inflorescences per crown. They can tolerate winter temperatures below −30° C. with a 10 cm straw mulch cover.

Plant characteristics

Plant:

*Height.*—Average 20 cm.
*Spread.*—Average 23 cm.
*Number of crowns.*—Average 4.
*Habit.*—Flat.
*Density (of individual plants in hill culture or plants/m² for matted rows).*—Open to medium.
*Vigor.*—Medium to strong.
*Low temperature tolerance.*—High.

Stolon characteristics

Stolon:

*Length.*—Average 70 cm.
*Number.*—Medium to many.
*Thickness.*—Medium to thick.

Fruit characteristics

'Saint-Jean d'Orléans' fruits, fruit production and fruit quality characteristics.

TABLE 1

Cumulative yield ($gm^{-1}$ of row), fruit weight, firmness, flavor, skin color, shelf life at room temperature and ripening season of 'Saint-Jean d'Orléans' as compared to 'Kent' Averages of four replicates from 2002 harvest

| Genotypes | Total yield ($g/m^{-1}$)[z] | Wt./fruit (g)[z] | Firmness[y] | Flavor[y] |
|---|---|---|---|---|
| Saint-Jean d'Orléans | 12712.1 | 8.8 | 3.7 | 3.6 |
| Kent | 8403.6 | 8.2 | 2.8 | 4.0 |
| Prob ≦ 0.05 | ** | Ns | * | Ns |

| Genotypes | Skin color[y] | Shelf life at 20° C.[x] | Ripening season[w] |
|---|---|---|---|
| Saint-Jean d'Orléans | 2.2 | 4.0 | EM |
| Kent | 3.4 | 1.5 | EM |
| Prob ≦ 0.05 | * | * | — |

[z]Data taken from a 1-meter long representative portion of a 2-meter matted row (width 50 cm).
[y]Data were transformed to arcsin prior to analysis of variance (SAS institute, 1988)[2].
Firmness: 1 = very soft, 5 = very firm
Flavor: 1 = poor, 5 = excellent
Skin color: 1 = very pale, 5 = dark red
[x]Number of days at room temperature (20° C.) for which the fruits were more than 95% marketable.
[w]EM = Early-Midseason.
Significance: **0.01, *0.05, Ns not significant

TABLE 2

Antioxidant capacity and total phenolic content of 'Saint-Jean d'Orléans' mature fruit in comparison with 'Kent' Data collected in L'Acadie site (Québec)

| Genotype | Total antioxidant capacity TEAC[a] ($\mu mol.mg^{-1}$) crude | aqueous | lipophillc | FRAP[b] (μM) crude | Content Total phenols[c] (ppm) crude |
|---|---|---|---|---|---|
| Saint-Jean d'Orléans | 227.4 | 234.7 | 29.5 | 2044.9 | 107.8 |
| Kent | 198.8 | 228.6 | 29.6 | 2131.5 | 106.1 |
| Least Significant Difference (LSD) | 65.0 | 54.9 | 9.6 | 466.4 | 42.1 |

[a]TEAC: Trolox Equivalent Antioxidant Capacity expressed as μmol Trolox equivalent $mg^{-1}$ dry weight
[b]FRAP: Ferric-Reducing Antioxidant expressed as μM FRAP
[c]Total phenols expressed as ppm gallic acid equivalent.

Fruit:

*Ratio of length/maximum width.*—As long as broad.
*Length.*—Average 2.9 cm.
*Diameter.*—Average 3.2 cm.
*Predominant shape.*—Globose conic.

*Difference in shape between primary and secondary fruits.*—Slight.
*Band without achenes.*—Medium.
*Size of hollow center.*—None.
*Unevenness of surface.*—Weak.
*Skin color.*—RHS 43A.
*Evenness of color.*—Slightly uneven to even.
*Glossiness.*—Strong.
*Insertion of achenes.*—Below the surface of the fruit.
*Color of achenes.*—RHS 150C.
*Insertion of calyx.*—Level to the fruit.
*Attitude of the calyx segments.*—Flat to slightly reflexed.
*Size of the calyx in relation to fruit diameter.*—Same size.
*Adherence of the calyx.*—Strong.
*Firmness of flesh* (*when fully ripe*).—Firm.
*Color of flesh.*—RHS 43B.
*Evenness of color of flesh.*—Slightly uneven to even.
*Sweetness.*—Medium.
*Acidity.*—Medium.
*Time of flowering* (*50% of plants at first flower*).—Early.
*Harvest maturity* (*50% of plants with ripe fruits*).—Early.
*Type of bearing.*—Not everbearing.

'Saint-Jean d'Orléans' differs from its parents ('Joliette' and 'L'Acadie') in terms of fruit shape, calyx and total yield. As stated earlier, the 'Saint-Jean d'Orléans' fruit is globose-conic with slightly reflexed sepals, whereas the 'Joliette' fruit changes from globose to short-wedge shape during the harvest. 'Joliette' skin is reddish and its sepals are not reflexed but cover the fruit. 'L'Acadie' fruit is long conic with a white small neck under the calyx, whereas 'Saint-Jean d'Orléans' is short conic. The total yield of 'L'Acadie' (7696.3 kg/ha) is much lower than that of 'Saint-Jean d'Orléans'.

'Saint-Jean d'Orléans' produces perfect flowers, and attractive and medium size, light red to red, shiny fruits. The flesh is light to medium red almost throughout and very firm. Fresh fruits have a long shelf life and can maintain quality and appearance for up to 4–5 days at room temperature, making it superior to 'Kent' for shipping. 'Saint-Jean d'Orléans' produces a higher yield than 'Kent'. 'Saint-Jean d'Orléans' is also firmer than 'Kent', with similar flavor but lighter skin color.

'Saint-Jean d'Orléans' is an early mid-season cultivar (Table 1). Fifty percent of the primary fruit ripen by June 27 which is similar to 'Kent' at our substation in L'Acadie and the production peaks were reached on the same day as 'Kent'.

Chemical analysis of the fruits using HPLC[3] revealed that 'Saint-Jean d'Orléans' was higher in hydroxycinnamic acids (7.1 ppm p-coumaric acid equivalent), benzoic acids (14 ppm gallic acid equivalent) and flavonols (7.2 ppm quercetin-3-galactoside equivalent). The total phenolic content measured according to Slinkard and Singleton[4] was 107.8 ppm gallic acid equivalent; while total anthocyanins was 60.6 ppm cyanidins-3-galactoside equivalent, and ellagic acid was 2.3 ppm. All concentrations except the total anthocyanins and ellagic acid were higher than 'Kent' cultivar (4 ppm, 10.7 ppm, 4.2 ppm, 106 ppm, 103.8 ppm,3.9 ppm, respectively). However, the total antioxidant capacity (TEAC and FRAP) of different extracts measured as described by Gao et al.[5] and Tsao et al.[6] showed that 'Saint-Jean d'Orléans' was not significantly different from that recorded by 'Kent' (Table 2).

It seems that good storageability, firmness and low susceptibility to diseases of 'Saint-Jean d'Orléans' might be due only to the content of some phenolic components rather than to total phenolics. The same can be said about the antioxidant activity. According to Wang et al.[7] and Mayr et al.[8], phenolics were the main compounds involved in the effective defence of plant tissues against field and postharvest infection or injuries and were significantly more active individually than in combination. It has been shown that benzoic acids have antibacterial, antifungal and antioxidant properties to prevent food spoilage and to enhance quality and shelf life[9,10]. Lindhard Pedersen[11] found that resistance to the diseases of five black currant cultivars was correlated with their high levels of hydroxycinnamic acid derivatives. Moreover, these acids can react with organic molecules such as amino acids to and synthesize toxic secondary metabolites that become highly toxic to the pathogen[12].

Foliage characteristics

Leaf:
*Green color of upper side.*—RHS 137C.
*Green color of lower side.*—RHS 138C.
*Blistering* (*interveinal blisters*).—Very week to medium.
*Number of leaflets.*—Three.

Terminal leaflet:
*Length.*—Average 7.6 cm.
*Width.*—Average 7.7 cm.
*Profile.*—Cupped.
*Length/width ratio.*—As long as broad to longer than broad.
*Shape of base.*—Obtuse.
*Shape of teeth.*—Acute to obtuse.

Petiole:
*Length.*—Average 19 cm.
*Pubescence.*—Medium to medium dense.
*Pose of hairs.*—Outwards.
*Color.*—RHS 143C.
*Length of stipule.*—Average 2.1 cm.
*Texture of stipule.*—Smooth.

Flowers and Inflorescences characteristics

Inflorescence:
*Position relative to foliage.*—Below to level with.
*Attitude of fruiting trusses* (*at first picking*).—Semi erect.
*Length of fruiting trusses.*—Average 18 cm.

Flowers:
*Color.*—White (no RHS reference).
*Flower size.*—Average 2.8 cm.
*Color of calyx.*—RHS 141C.
*Diameter of calyx.*—Average 2.7 cm.
*Diameter of calyx relative to corolla.*—Smaller to same size.
*Diameter of inner calyx relative to outer* (*on secondary flowers*).—Same size to larger.
*Spacing of petals* (*secondary flowers with 5 to 6 petals*).—Touching.
*Petal length/width ratio* (*on secondary flowers*).—As long as broad to longer than broad.

'Saint-Jean d'Orléans' demonstrates a higher degree of resistance to leaf diseases as compared to 'Kent'. Its susceptibility to leaf scorch (*Diplocarpon earlina* Ell. & Ev.)

and leaf spot (*Mycosphaerella fragariae* (Tul.) Lindau) was ranked as moderate to low in trials conducted since 1997.

'Saint-Jean d'Orléans' plants perform very well in heavy or sandy soils in a matted row system. It is also adapted to the waiting bed system using plastic mulch.

Tests and trials

Tests and trials for 'Saint-Jean d'Orléans' were conducted in matted rows at an experimental farm in l'Acadie, Québec since 1997. A completely randomized design for four replicates (4 plots) was used to evaluate the selections. Each experimental unit was a 4-meter long plot, 50 cm wide. A representative 2 m section of the plot was used for data collection. The remainder was used as guard row.

REFERENCES

1. Khanizadeh, S., B. Thériault, O. Carisse and D. Buszard. 1999. *AC-L'Acadie Strawberry.* HortScience 34(4):743–744.
2. SAS Institute. 1988. *Statistical analysis system. SAS/STAT, SAS/BASIC guide for personal computers,* version 6.04 (ed). SAS Inst. Cary., N.C.
3. Tsao, R. and R. Yang. 2003. *Optimization of a new mobile phase to know the complex and real Polyphenolic composition: towards a total phenolic index using high-performance liquid chromatography.* J. Chromatogr. A. 1018:29–40.
4. Slinkard, K. and V. L. Singleton. 1977. *Total phenol analysis: automation and comparison with manual methods.* Am. J. Enol. Viticult. 28:49–55.
5. Gao, X., M. Ohlander, N. Jeppsson, L. Bjork and V. Trajkovski. 2000. *Changes in antioxidants effects and their relationship to phytonutrients of Sea Buckthorn (Hippophae rhamnoides L) during maturation.* J. Agric. Food Chem. 48:1485–1490.
6. Tsao, R., R. Yang and J. C. Yang. 2003. *Antioxidant isoflavones in Osage Orange, Maclura pomifera(Raf.) Schneid.* J. Agric. Food Chem. 51:6445–6451.
7. Wang, S. Y., J. L. Mass, J. A. Payne and G. Galleta. 1994. *Ellagic acid in small fruits, mayhaws, and other plants.* J. Small Fruit and Viticulture 2 (4): 39–49.
8. Mayr, U., Michalek, S., Treutter, D. and W. Feucht. 1997. *Phenolic compounds of apple and their relationship to scab resistance.* J. Phytopathology 145: 69–75.
9. Baldwin E. A., M. O. Nisperos-Carriedo and R. A. Baker. 1995. *Use of edible coatings to preserve quality of lightly processed products.* Crit. Rev. Food Sci. Nutr. 35:509–24.
10. Khan, S. H., J. Aked and N. Magan. 1995. *The potential for anti-oxidant chemicals to control Colletotrichum musae on banana fruit.* 51 International Symposium on Crop Protection. Gent (Belgium). V.64 (3b): 531–537.
11. Lindhard Pedersen. 2003. http://www.darcof.dk/research/darcofi/ii1.html
12. Nicholson, R. L., and R. Hammerschmidt. 1992. *Phenolic compounds and their role in disease resistance.* Annu. Review Phytopathology 30:369–389.

What is claimed is:

1. A new and distinct strawberry plant named 'Saint-Jean d'Orléans' as described and illustrated herein.

* * * * *